United States Patent
Gaessler et al.

(10) Patent No.: US 7,636,164 B2
(45) Date of Patent: Dec. 22, 2009

(54) DEVICE HAVING A FIELD MIRROR FOR OPTICALLY TESTING A SURFACE

(75) Inventors: Joachim Gaessler, Donaueschingen (DE); Christian Konz, Oehningen (DE); Harald Richter, Constance (DE)

(73) Assignee: Intelligente Optische Sensoren und Systeme GmbH, Radolfzell (DE)

( * ) Notice: Subject to any disclaimer, the term of this patent is extended or adjusted under 35 U.S.C. 154(b) by 49 days.

(21) Appl. No.: 12/117,236

(22) Filed: May 8, 2008

(65) Prior Publication Data

US 2008/0285020 A1    Nov. 20, 2008

(30) Foreign Application Priority Data

May 15, 2007    (DE) .................... 10 2007 022 831

(51) Int. Cl.
*G01N 21/55* (2006.01)
(52) U.S. Cl. .................... 356/445; 356/237.2
(58) Field of Classification Search ............. 356/445, 356/237.2
See application file for complete search history.

(56) References Cited

U.S. PATENT DOCUMENTS 4,561,722 A    12/1985    Smetana 6,870,949 B2    3/2005    Baldwin
7,199,877 B2 *    4/2007    Kehoe et al. ................ 356/328

FOREIGN PATENT DOCUMENTS

| DE | 38 38 954 | 5/1990 |
| DE | 44 34 699 | 4/1996 |
| DE | 20 2006 017 | 4/2007 |
| JP | 08 172506 | 7/1996 |

OTHER PUBLICATIONS

Examination Report, DE 10 2007 022 831.9, dated Apr. 14, 2008.

* cited by examiner

*Primary Examiner*—Roy Punnoose
(74) *Attorney, Agent, or Firm*—Knobbe, Martens, Olson & Bear LLP

(57) ABSTRACT

The invention generally relates to a compact, inexpensive-to-manufacture device consisting of few components for optically testing a surface. The zone on the surface that is to be investigated is illuminated by a semitransparent mirror and an aspheric field mirror, employing a telecentric optical train, and at least part of the light reflected or scattered by the surface is imaged onto the entrance pupil of the lens of an electronic camera by the field mirror, via the semitransparent mirror. Images recorded by the camera are analyzed using known image-processing methods.

9 Claims, 2 Drawing Sheets

DEVICE HAVING A FIELD MIRROR FOR OPTICALLY TESTING A SURFACE

CROSS-REFERENCE TO RELATED APPLICATIONS

This Application claims the benefit of German Application DE 10 2007 022 831.9 filed May 15, 2007, which is hereby incorporated by reference in its entirety.

BACKGROUND OF THE INVENTION

1. Field of the Invention

The invention generally relates to a device and a method for optically testing a surface.

2. Description of the Related Art

An image-recording device for imaging flaws on a planar, reflective surface, where a telecentric optical train is employed for imaging that zone of the surface to be investigated using a camera is described in U.S. Pat. No. 6,870,949B2. The '949 patent describes the dark-field illumination of the surface as being provided by an annular illumination source arranged coaxial to the camera's optical axis. That device also provides that light from the light sources for illuminating surfaces is reflected normal to the camera's optical axis by a semitransparent mirror, in which case, facilities for implementing bright-field illumination are also provided. In the latter case, the illuminated spot on the surface under investigation is imaged onto the camera lens by the field lens and the beam path transits the semitransparent-mirror's plane-parallel plate, thereby causing astigmatism that reduces image fidelity, particularly in the case of large beam divergences, such as whenever field lenses having short focal lengths are employed.

A beam splitter for an illumination-side and sensor-side, telecentric, optical train that provides for at least a transparent masking of the semitransparent mirror in order to prevent stray-light effects due to the presence of contamination is described in U.S. Pat. No. 4,561,722A.

A manuscript reader having a camera and nearly on-axis, dark-field illumination, where the same telecentric lens is used for illumination and the camera's optical train, is described in Japanese patent application JP 08172506A. Its nearly on-axis, dark-field illumination yields improved character recognition, particularly on glossy paper.

The arrangements having a camera whose lens lies on the axis of the telecentric optical train that are described in U.S. Pat. No. 6,870,949B2 and JP 08172506A have the disadvantage that the heights of the entire arrangements, as measured along their field lens' optical axis, exceed their field lens' focal length by more than the overall length of their camera and camera lens.

Common to all arrangements that employ field lenses is that reflections that may be optimally suppressed only over a narrow wavelength range by coating their surfaces occur at the front and rear surfaces thereof. Chromatic aberration that can be only partially avoided by employing expensive, achromatic, lens systems occurs, particularly in cases where polychromatic light is used for investigating surfaces. Furthermore, more often than not, all arrangements that employ telecentric optical trains have undesirably large heights, as measured normal to the surfaces under investigation, which can present problems, particularly in cases where space in the vicinities of those surfaces is at a premium. Even employing a planar, beam-deflecting mirror between those surfaces and the field lens may frequently be insufficient to allow adequately reducing the dimensions of overall arrangements, as measured normal to the surfaces under investigation.

Preferred embodiments of the invention shall be described in detail below, based on the accompanying figures.

SUMMARY OF THE INVENTION

One of the problems addressed by the invention is that of creating a compact, inexpensive-to-manufacture device which includes few components for optically testing an essentially rectangular zone on a diffusely reflective, or specularly reflective, surface, employing a telecentric optical train for light having various wavelengths, where the device, in certain preferred embodiments, should have the minimum height possible, particularly as measured normal to the surface under investigation. In particular, the term "optical testing" is a broad terms and shall have its ordinary meaning and shall include, but not be limited to, both the qualitative detection of surface textures and/or flaws and character and/or code-symbol recognition.

An embodiment of the invention solves that problem by employing an aspheric field mirror having a short focal length to image light emanating from the surface under investigation onto the entrance pupil of the lens of an electronic camera, via a semitransparent mirror, where, in the case of bright-field illumination, the surface involved is illuminated by a light source that is preferably configured in the form of a ground glass plate irradiated by a monochromatic, or polychromatic, semiconductor light source arranged in the field-mirror's focal plane, in the vicinity of the field-mirror's optical axis.

DETAILED DESCRIPTION OF THE PREFERRED EMBODIMENT

Figure 1:
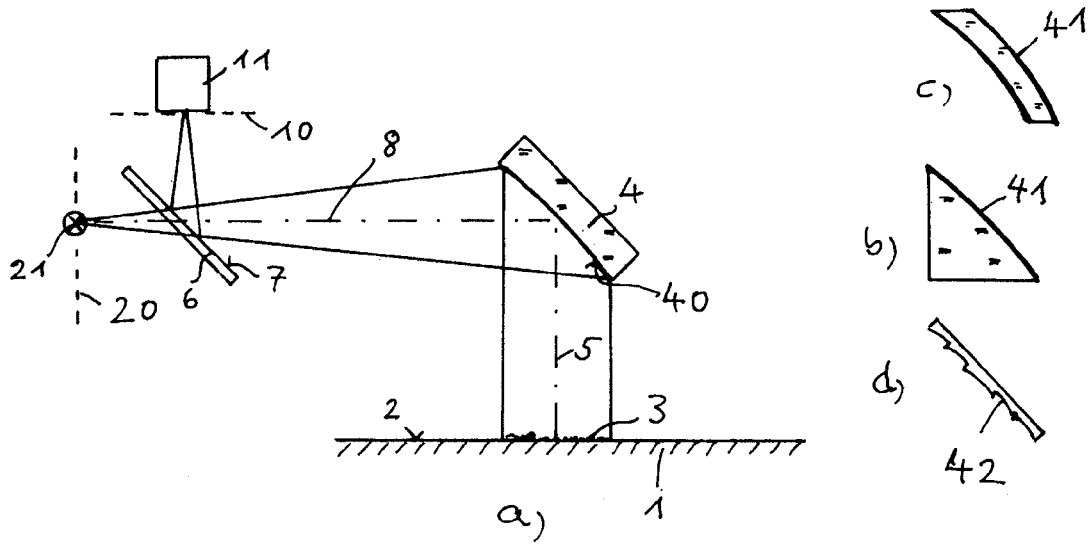
FIG. 1A is a schematic depiction of an optical train of one preferred embodiment of the present invention, as viewed normal to the optical axes of the camera lens and field mirror
FIG. 1B is a schematic illustration of a rear-surface field mirror of one preferred embodiment including a prism
FIG. 1C is a schematic illustration of a rear-surface field mirror of one preferred embodiment
FIG. 1D is a schematic illustration of a field mirror of one preferred embodiment having a Fresnel surface figure

FIG. 1A schematically depicts an optical train according to a preferred embodiment of the invention, as viewed normal to the optical axis of the camera 11, and the telecentric field mirror 4. The field mirror 4, which is shown here in a sectional view, has a cross-section, projected along the optical axis 5, that includes the perimeter of the zone 3 of the surface 2 that is to be investigated. A special feature of telecentric optical trains is that the field mirror 4 yields parallel ray paths on that side thereof facing the zone 3 to be investigated, and the projection of the field mirror 4 along the optical axis 5 in some embodiments must, therefore, contain the zone to be investigated. In certain preferred embodiments, the telecentric image of the zone 3 to be investigated reproduces the texturing thereof, regardless of the distance between the field mirror 4 and the surface 2, with the same magnification in all cases. Telecentric imaging optics are thus the preferred choice on systems for handling optical-metrology tasks. In some embodiments, the divergence angle of the telecentric ray bundle should be chosen as large as possible in order to achieve at a short overall length, as measured along the optical axis 8 of the field mirror 4. Since large divergence angles lead to severe imaging errors in the case of optical trains containing spherical optical components, it is provided that the field mirror 4 of a preferred embodiment is configured in the form of an aspheric mirror. The field mirror 4 is preferably fabricated from glass that has been ground and coated such that it has an aspheric figure over at least part, or parts, of its reflective surface. The reflective coating involved may be either a front-surface reflective coating 40 or a rear-surface reflective coating 41, where the term "front-surface reflective coating" 40 is a broad terms and shall have its ordinary meaning and shall include, but not be limited to, a reflective coating that reflects light rays from the interface between the ambient air and the mirror, and the term "rear-surface reflective coating" 41 is a broad term and shall have its ordinary meaning and shall include, but not be limited to, a reflective coating that reflects light rays from an interface between the mirror's glass body and its reflective coating. An example of a front-surface reflective coating 40 is those used on concave, aspheric, metal mirrors, such as those employed in cases where surfaces 2 are to be investigated using light having wavelengths falling within the infrared spectral region.

As schematically depicted in FIGS. 1B and 1C, a prism having a pair of mutually orthogonal, intersecting surfaces or a body having a concave surface and a convex surface are shown. where the rear, convex surface of the latter is aspheric and has a reflective coating, is provided as a support for the field mirror 4 in the case of a field mirror 4 having a rear-surface reflective coating 41 on an aspheric, reflective, outer surface. In conjunction with certain embodiments of the invention, it is also contemplated that the field mirror 4 be fabricated from plastic employing an injection-molding process. In FIG. 1D, the field mirror provided is in the form of a Fresnel mirror 42, where at least part, or parts, of the Fresnel mirror 42 has/have an aspheric, reflectively coated surface.

Light emanating from the zone 3 to be investigated parallel to the optical axis 5 of the field mirror 4 is imaged onto the focal plane 10 of the field mirror 4 by a beam splitter 6 having a partially transmitting, reflective surface 7 arranged at an angle of about 45° with respect to the camera-side optical axis 8 of the field mirror 4. The entrance pupil 13 of the lens of a camera 11 is arranged in the focal plane 10 such that the image of an object point on the surface 2 lying on the optical axis 5 of the field mirror 4 will be imaged at the center of the entrance pupil 13. The camera 11 involved is preferably an electronic camera equipped with a CCD or CMOS image-acquisition device arranged on a camera board, which is not shown. The camera board preferably contains electronic circuitry for controlling the camera 11, in particular, circuitry for controlling image-acquisition and readout operations.

A light source 21 for the bright-field illumination of the zone 3 to be investigated is arranged on the extension of the optical axis 8 of the field mirror 4, in the focal plane 20 of the field mirror 4.

Figure 2:
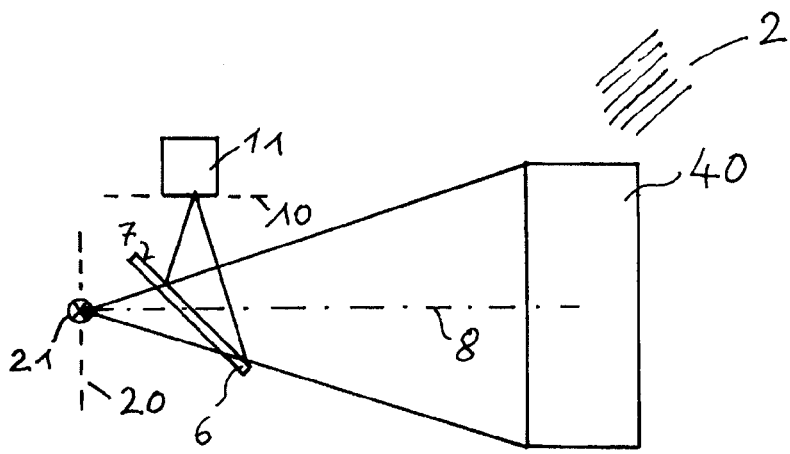
FIG. 2 is a schematic illustration of a device according to one preferred embodiment of the invention, as viewed along the field mirror's optical axis (5)

FIG. 2 schematically depicts an embodiment of the arrangement according to an embodiment of the invention where the optical axis of the lens of the camera 11 is parallel to the surface 2 of the substrate 1, which further reduces the overall height of the device, as measured normal to the surface 2, compared to the embodiment of the arrangement shown in FIG. 1A.

Figure 3:
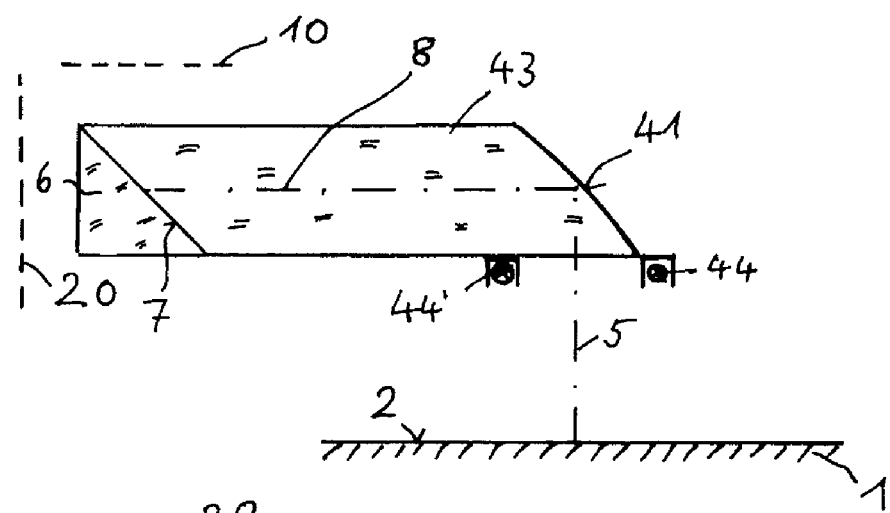
FIG. 3 is a schematic, sectional view of a device according to one preferred embodiment of the invention having a glass body

FIG. 3 depicts a schematic, sectional view of a compact arrangement according to a preferred embodiment of the invention where the field mirror having a rear-surface reflective coating 41 and the partially transmitting, reflective surface 7 form a unit. A beam splitter 6 is cemented onto the partially transmitting, reflective surface 7. A glass body 43 that, as in the case of the rear-surface, reflective coating 41 and partially transmitting, reflective surface 7, has a planar surface, through which light from the surface 2 under investigation enters the glass body 43 or exits from the glass body 43 along a direction leading toward the camera, which is not shown here, that is situated in the focal plane 10 of the field mirror 4, is provided. Boundary surfaces of the glass body 43 that represent no optical components in the sense of the arrangement according to certain embodiments of the invention are preferably coated with light-tight, absorbing coatings.

Figure 4:
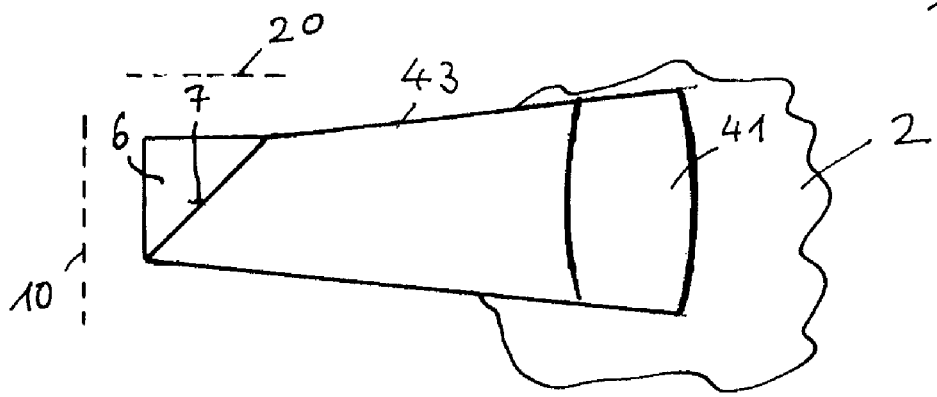
FIG. 4 is a top view of a device according to one preferred embodiment of the invention having a glass body.

FIG. 4 depicts a top view, showing a view along the normal to the surface 2 under investigation, of an arrangement having a glass body 43, where the camera and the illumination optical train have been interchanged, relative to the arrangement shown in FIG. 3, which yields a particularly low overall height of the arrangement, as measured normal to the surface 2 under investigation, where the entrance pupil of the camera, which is not shown here, is provided in the focal plane 20 and the light source, which is also not shown here, is provided in the focal plane 20. The optical train of the arrangement shown in FIG. 4 may also be implemented using the optical components, i.e., the field mirror 4 and beam splitter 6, shown in FIG. 1.

The arrangements shown in FIGS. 3 and 4 have certain advantages such as that no surfaces that might be affected by environmental factors, for example, might accumulate dust, are present between the rear-surface, reflective coating 41 and the partially transmitting, reflective surface 7.

The glass body 43 shown in FIG. 3 may be extended out to the focal plane 10, if necessary, in which case, a light source having an index-matching adhesive is attached directly to the surface of the glass body 43. It is also provided that a CCD camera chip may be cemented directly onto the surface of the glass body 43 using an index-matching adhesive in the event that the camera and illumination optical trains are interchanged.

Any of the optical components involved, such as the glass body 43, the beam splitter 6, or the field mirror 4, may be fabricated from either glass or polymers. The field mirror may also be configured in the form of a metal mirror.

The light source 21 may be configured in the form of a point source situated in the focal plane 20 and on the optical axis 8 shown in FIG. 1 in order to provide bright-field illumination. The preferred embodiments of the invention provide that further light sources, or a spatially extended light source, may be arranged in the focal plane 20, or in the vicinity thereof. A point-source light source situated in the focal plane 20 may be replaced by a slightly spatially extended light source situated in the vicinity of the focal plane 20, depending upon the metrological task involved and the properties of the surface 2 under investigation. It is provided that the luminous intensities, the composite color of the emitted light, and the spatial distributions of the intensities and wavelengths of the light source 21, or of the arrangement consisting of several light sources, may be adjusted using an illumination controller, which shall not be described in greater detail here.

It is also provided that a supplementary light source 44 may be arranged on that side of the field mirror facing the surface 2 under investigation, outside the telecentric ray bundle. An example thereof is depicted in FIG. 3.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner in one or more embodiments, as would be apparent to one of ordinary skill in the art from this disclosure. Additionally, although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A device for optically testing a zone of a specularly reflective or diffusely reflective surface of a substrate that is to be investigated, comprising:
   a field mirror having a substrate-side optical axis normal to the surface and a camera optical axis;
   at least one light source for providing bright-field illumination arranged on the camera-side optical axis, in the vicinity of the focal plane of the field mirror, that is imaged onto the zone that is to be investigated employing a telecentric optical train; and
   an electronic camera whose entrance pupil lies in the focal plane of the field mirror, on the camera-side optical axis, and receives part of the light emanating from the zone on the surface that is to be investigated via a telecentric optical train and transmits the images obtained to a processing device,
   wherein the field mirror has an aspheric, reflective surface, where the beam projected onto the surface under investigation at least covers just the zone that is to be investigated and where the camera-side optical axis is inclined at an angle of about 55° to 90° to the substrate-side optical axis and wherein a beam splitter that splits a central ray traveling along the camera-side optical axis into a transmitted ray and a ray reflected through 90° is arranged on the camera-side optical axis, and the camera is arranged on one of the pair of beam axes and the light source is arranged on the other beam axis.

2. A device for optically testing a surface according to claim 1, wherein at least one other light source that may be operated either jointly with the light source, or alone, controlled by an illumination controller, is arranged near the focal plane, in the vicinity of the light source.

3. A device for optically testing a surface according to claim 2, wherein the other light source is configured in the form of a spatially extended light source surrounding the light source.

4. A device for optically testing a surface according to claim 2, wherein the other light source is configured in the form of an array of numerous, individual, essentially point light sources, where the individual light sources may be independently controlled by the illumination controller.

5. A device for optically testing a surface according to claim 1, wherein the functions of the field mirror and beam splitter are incorporated into a compact, glass body that has a reflective coating on its rear surface and a partially transmitting, reflective surface.

6. A device for optically testing a surface according to claim 1, wherein the field mirror and the glass body are injection-molded, plastic components.

7. A device for optically testing a surface according to claim 1, wherein the light source is configured in the form of an optically active component having a controllable micro-mirror array.

8. A device for optically testing a surface according to claim 1, wherein the field mirror is configured in the form of a Fresnel mirror.

9. A method for optically testing a surface according to claim 1, wherein a supplementary light source for illuminating the zone that is to be investigated is arranged outside the telecentric ray bundle, between the zone that is to be investigated and the field mirror, and the supplementary light source may be controlled either alone, or jointly with other light sources.

* * * * *